United States Patent
Garcia et al.

[11] Patent Number: 5,116,849
[45] Date of Patent: May 26, 1992

[54] 4-AMIDINO CHROMAN AND 4-AMIDINO PYRANO (3,2-C) PYRIDINE DERIVATIVES, A PROCESS FOR THEIR PREPARATION AND PHARMACEUTICAL COMPOSITIONS CONTAINING THEM

[75] Inventors: Georges Garcia, Saint-Gely-du-Fesc; Patrick Gautier, Cournonterral; Dino Nisato, Saint-Georges d'Orques; Richard Roux, Vailhauques, all of France

[73] Assignee: Sanofi, Paris, France

[21] Appl. No.: 606,864

[22] Filed: Oct. 31, 1990

[30] Foreign Application Priority Data

Nov. 6, 1989 [FR] France ................. 89 14518
Feb. 2, 1990 [FR] France ................. 90 01258

[51] Int. Cl.$^5$ .............. A61K 31/44; C07D 407/04
[52] U.S. Cl. ........................ 514/337; 514/302; 514/275; 546/269; 546/115; 546/116; 546/22; 544/331; 544/297
[58] Field of Search ................ 546/269; 514/337

[56] References Cited

FOREIGN PATENT DOCUMENTS 0205292 12/1986 European Pat. Off.
0296975 12/1988 European Pat. Off.
0312432 4/1989 European Pat. Off.

OTHER PUBLICATIONS

Bergmann et al., CA112:55531k.
Shiokawa et al. CA113:6361s
Stenzel et al. CA113:78160y.

Primary Examiner—Jane T. Fan
Attorney, Agent, or Firm—Bacon & Thomas

[57] ABSTRACT

The present invention deals with 4-amidino chroman and 4-amidino pyrano (3,2-c) pyridine derivatives, a process for their preparation and pharmaceutical compositions containing them. Said derivatives have antihypertensive and antiarrhythmic activities. They respond to formula

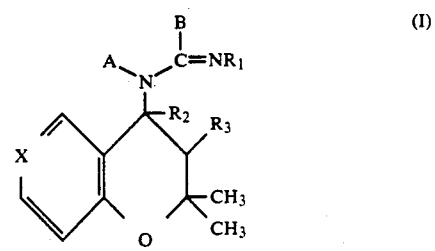

in which:
A+B=—CH=CH—CH=N— or —CH=C-$R_4$—C$R_5$=CH—;
X=N, N→O, C—Z;
$R_1$=H, CN, $NO_2$, $C_1$-$C_4$ alkyl, OH, $C_1$-$C_4$ alkoxy, $CF_3CO$—, $CH_3$—$SO_2$—, $\phi$—$SO_2$—;
$R_2$=H;
$R_3$=OH or $OCOCH_3$ or $R_2+R_3$=double bond.

15 Claims, No Drawings

4-AMIDINO CHROMAN AND 4-AMIDINO PYRANO (3,2-C) PYRIDINE DERIVATIVES, A PROCESS FOR THEIR PREPARATION AND PHARMACEUTICAL COMPOSITIONS CONTAINING THEM

The object of the present invention is 4-amidino chroman and 4-amidino pyrano(3,2-c)pyridine derivatives, a process for their preparation and pharmaceutical compositions containing them. The said derivatives have antihypertensive and antiarrhythmic activities.

The Belgian patent 829 611 mentions a whole series of derivatives of 3-chromanol with antihypertensive activity; these derivatives are characterized by the presence at position 4 of a $NR_1R_2$ group in which $R_1$ is a hydrogen or an optionally substituted hydrocarbon group, $R_2$ is hydrogen or an alkyl, $NR_1R_2$ being optionally a heterocyclic group containing from 3 to 8 atoms, unsubstituted or substituted by one or two methyl groups and by the optional presence of a large number of possible substituents at position 6 or at position 7.

The European patent application No. 273 262 describes chroman derivatives of formula:

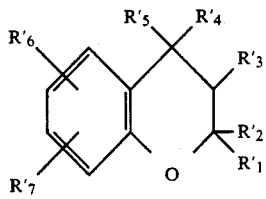

in which in particular:

$R'_5$ denotes a heterocyclic group such as 2-pyridon-1-yl, 2-pyridazinon-1-yl, 2-pyrimidon-1-yl, 6-pyrimidon-1-yl, 2-pyrazinon-1-yl, 2-thiopyridon-1-yl; this group being partially hydrated, substituted or unsubstituted;

$R'_3$ represents OH or $OCOCH_3$;

$R'_4$ represents hydrogen or else $R'_3$ and $R'_4$ together form a bond.

The European patent applications 296 975 and 312 432 describe similar compounds.

Finally, the European patent application 205 292 describes pyrano[3,2-c]pyridine derivatives of formula:

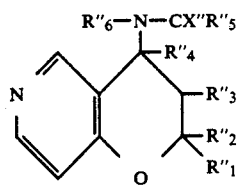

in which $X''$ represents O or S and $R''_5$ and $R''_6$ may form a heterocycle.

Novel compounds, chroman and pyrano(3,2-c)pyridine derivatives, have now been found which possess activity as antihypertensive and antiarrhythmic agents.

Thus, in respect to one of its features, the present invention relates to compounds of formula:

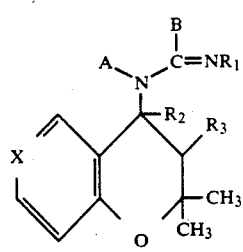

in which:

A and B are linked together between N and $C=NR_1$ and represent
either a $-CH=CH-CH=N-$ group
or a $-CH=CR_4-CR_5=CH-$ group, one of the substituents $R_4$ or $R_5$ denoting hydrogen, the other being selected from hydrogen, halogen, nitro or $C_1-C_4$ alkyl;

X represents a nitrogen atom, a N-oxide group or the C—Z group;

Z represents hydrogen, halogen, $C_1-C_4$ alkyl, cyano, nitro, acetyl or trifluoroacetyl, phosphono or dialkoxyphosphoryl in which the alkyl is a $C_1-C_3$ group or an amino group;

$R_1$ represents hydrogen, cyano, nitro, $C_1-C_4$ alkyl, hydroxyl, $C_1-C_4$ alkoxy, trifluoroacetyl, methanesulfonyl, benzenesulfonyl unsubstituted or substituted on the phenyl by methyl, halogen or trifluoromethyl;

$R_2$ represents hydrogen;

$R_3$ represents hydroxyl or acetyloxy or $R_2$ and $R_3$ together form a bond.

In the present description and in the claims which follow, halogen means a chlorine, bromine or fluorine atom.

The compounds of formula (I) in which $R_2=H$ and $R_3=OH$ or $OCOCH_3$ have the trans configuration. They may contain two asymmetric carbon atoms. The present invention includes each of the optical isomers of the compounds of formula (I) as well as the racemate.

Another object of the present invention is a process for the preparation of the compounds (I).

The said process is characterized in that:

a) an epoxide II of formula:

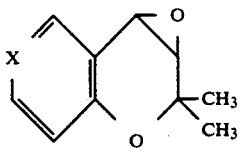

in which X has the meanings given above in the case of I, is treated with a heterocycle III corresponding to one of the following tautomeric forms:

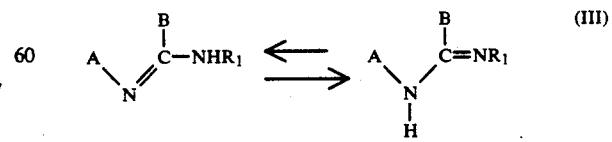

in which A, B and $R_1$ have the meanings previously indicated for (I):

b) acetic anhydride is optionally reacted with the compound obtained of formula (I) in which $R_2=H$ and $R_3$=OH in order to prepare the compound of formula (I) in which $R_2$=H and $R_3$=—OCOCH$_3$;

c) the compound obtained in step a) of formula (I) in which $R_2$=H and $R_3$=OH or the compound obtained in step b) of formula (I) in which $R_2$=H and $R_3$=OCOCH$_3$ is optionally treated in order to prepare a compound of formula (I) in which $R_2$ and $R_3$ together form a bond.

In step (a), the epoxide (II) ring-opening reaction is conducted at a temperature between 10° C. and 100° C. in an inert organic solvent such as dioxane, tetrahydrofuran, methyl-tert.-butyl ether, dimethylsulfoxide or dimethylformamide in the presence of a basic condensing agent such as sodium hydride, triethylamine, a quaternary ammonium hydroxide such as benzyltrimethylammonium hydroxide. Under such operating conditions, the opening of the epoxide (II) leads to compounds of formula (I) having the trans configuration in which $R_2$=H and $R_3$=OH.

In step b), the acetylation is performed at a temperature between 20° and 100° C. for a period varying from 1 to 48 hours in a basic solvent such as pyridine or triethylamine.

In step c), the dehydration of the compound prepared in step a) is obtained by reaction of an alkali hydride, for example sodium hydride or lithium hydride, in an inert solvent at a temperature between 20° C. and 100° C.; the deacetylation of the compound prepared in step b) is effected in the presence of diazabicycloundecene by heating between 50° and 110° C. in an inert solvent such as toluene or benzene.

The epoxides of formula (II) are known or prepared according to known methods.

The epoxide (II) in which X represents a nitrogen atom is described in the European patent application 205 292. The epoxide (II) in which X represents a N-oxide group is described in the application WO 89/10925. The epoxides (II) in which X represents the C—Z group are described in various publications.

Thus, the epoxide (II) in which Z represents the cyano group is described in the Belgian patent 852 955; the epoxide (II) in which Z represents the nitro group or an acetyl group is described in J. Med. Chem., 1983, 23, 1582-1589; the epoxides (II) in which Z represents a halogen are prepared according to Tetrahedron, 1981, 37 (15), 2613-2616. The epoxides (II) in which Z represents the trifluoroacetyl or a phosphono group or a dialkoxyphosphoryl group in which the alkyl is $C_1$-$C_3$ are described in the European patent application 296 975. The epoxide (II) in which Z represents hydrogen is described in J. Chem. Soc., 1962, 76-79. The epoxide (II) in which Z is a methyl is described in Aust. J. Chem. 1979, 32 (3), 619-636; when Z represents a $C_2$-$C_4$ alkyl, the epoxide (II) is obtained in an analogous manner. Finally, the epoxide (II) in which Z represents a NH$_2$ group is described in the European patent application 273 262. It may also be obtained by reduction of the epoxide (II) in which Z represents NO$_2$.

The heterocyclic compounds (III) are known or prepared by known methods. In particular, in the case of the preparation of the cyanamino pyridines or pyrimidines, the method described in Ann. Pharm. Fr., 1968, 26 (6), 469-472 may be used. The sulfonamino pyridines are described in Doklady Akad. Nauk. S.S.S.R., 1957, 113, 1080-3. They may be prepared by reaction of the appropriate sulfornyl derivative on the aminopyridine. Moreover, standard methods of organic chemistry have been applied to the preparation of some compounds (III). Thus, the compounds (III) in which $R_1$ is a nitro group are used to prepare the compounds (III) in which $R_1$ is a $C_1$-$C_4$ alkyl by reaction with a $C_1$-$C_4$ alkylamine in basic medium. Said compounds (III) in which $R_1$ is a nitro group may also be used to prepare the compounds (III) in which $R_1$ is a hydroxyl group by reaction with hydroxylamine. The pyridylnitramines ($R_1$=NO$_2$) are prepared according to J. Am. Chem. Soc., 1955, 77, 3154-3155.

The compounds according to the invention increase the polarization of the smooth muscle fibers and have a vasodilator effect on the portal vein according to the assays described in the European patent application 296 975. Their antihypertensive effect was observed in animals.

Furthermore, it has been observed that the compounds according to the invention accelerate the repolarization of the myocardial cells; at the same time, their antiarrhythmic effect has been observed in an animal model.

No sign of toxicity is observed with these compounds at pharmacologically active doses.

Thus, the compounds according to the invention may be used in the treatment of hypertension, pathological disorders associated with the contraction of the smooth muscle fibers of the gastrointestinal, respiratory, uterine and urinary apparatuses, for example: ulcers, asthma, premature uterine contraction, incontinence, and in the treatment of other cardiovascular diseases such as: angina pectoris, cardiac insufficiency, cerebral and peripheral vascular diseases. In addition, the compounds according to the invention may be used in the treatment of cardiac arrhythmia as well as in the treatment of glaucoma. Moreover, the compounds according to the invention may be used in the treatment of depression or other diseases of the central nervous system, such as epilepsy.

Finally, the compounds of the present invention may be used for the topical treatment of alopecia.

Thus, another object of the present invention is pharmaceutical compositions containing an effective dose of one compound according to the invention and suitable excipients. The said excipients are selected according to the pharmaceutical form and the mode of administration desired.

In the pharmaceutical compositions of the present invention for oral, sublingual, subcutaneous, intramuscular, intravenous, topical, transdermal or rectal administration, the active ingredients of formula (I) above, may be administered in dosage unit forms of administration mixed with standard pharmaceutical vehicles to animals or humans for the prophylaxis or treatment of the above disorders and diseases. Suitable specific forms of administration include the forms for the oral route such as tablets, capsules, powders, granules and oral solutions or suspensions, buccal and sublingual forms of administration, subcutaneous, intramuscular or intravenous forms of administration and rectal forms of administration. For topical application, the compounds according to the invention may be used in creams, ointments or lotions.

In order to produce the desired prophylactic or therapeutic effect, the dose of the active ingredient may be varied between 0.01 and 1 mg per kg of body weight and per day.

Each unit dose may contain from 0.01 to 2 mg, and preferably from 0.02 to 1 mg of active ingredients in combination with a pharmaceutical vehicle. This unit dose may be administered 1 to 5 times per day so as to provide a daily dose of from 0.01 to 10 mg, and preferably from 0.02 to 5 mg.

When a solid composition is prepared in the form of tablets, the principal active ingredient is mixed with a pharmaceutical vehicle such as gelatin, starch, lactose, magnesium stearate, talc, gum arabic or similar substances. The tablets may be coated with sucrose, a cellulose derivative, or other suitable materials or they may even be treated so that they have a sustained or delayed activity and continuously release a predetermined amount of active ingredient.

A preparation in capsular form is produced by mixing the active ingredient with a diluent and pouring the mixture obtained into soft or hard capsules.

A preparation in the form of a syrup or an elixir or for administration in the form of drops may contain the active ingredient together with a sweetener, preferably calorie-free, methylparaben and propylparaben as antiseptics, as well as an agent conferring taste and a suitable colouring matter.

The powders or granules dispersible in water may contain the active ingredient mixed with dispersing agents or wetting agents or suspending agents such as polyvinylpyrrolidone as well as with sweeteners or taste modifiers.

In the case of rectal administration, suppositories are used which are prepared with binders melting at the rectal temperature, for example cocoa butter or polyethylene glycols.

For parenteral administration, aqueous suspensions, isotonic saline solutions or sterile and injectable solutions which contain pharmacologically compatible wetting and/or dispersing agents, for example propylene glycol or butylene glycol, are used.

The active ingredient may also be formulated in the form of microcapsules, optionally with or without one or more additives or supports.

The compositions of the present invention may contain, in addition to the products of formula I above, or one of their pharmaceutically acceptable salts, other active ingredients such as, for example, tranquilisers, beta-blockers or other medicines which may be useful in the treatment of the disorders or diseases indicated above.

The following examples illustrate the invention without in any way limiting it. In the examples as well as in the descriptive part and in the claims, some products are designated as derivatives of chroman. It is understood that said products of the present invention are derivatives of 2,2-dimethyl 3,4-dihydro 2H-chromene and that the term "chroman" designates "3,4-dihydro 2H-chromene".

The melting points (Mp) are given in degrees centigrade.

EXAMPLE 1

Trans 4-(2-cyanimino 1,2-dihydro 1-pyridyl) 6-cyano 2,2-dimethyl 3-hydroxy chroman: SR 47023
(A+B=—CH=CH—CH=CH—; X=C—CN; $R_1$=CN; $R_2$=H; $R_3$=OH)

2-Cyanamino pyridine is prepared according to the method described in Ann. Pharm. Fr., 1968, 26 (6), 469-472.

A solution containing 1 g of 6-cyano 2,2-dimethyl 4,4-epoxy chroman, 0.8 g of 2-cyanamino pyridine in 50 ml of dimethoxyethane and 0.2 ml of benzyltrimethylammonium hydroxide is heated at reflux for 24 hours. The reaction mixture is concentrated, and the residue is taken up in 50 ml of water and extracted twice with ethyl acetate. The extracts are dried over sodium sulfate and concentrated. The residue is taken up in ethyl ether, filtered off and washed with dichloromethane. 110 mg of the expected product are obtained.
Mp=284° C.

EXAMPLE 2

Trans 4-(2-cyanimino 1,2-dihydro 1-pyridyl) 2,2-dimethyl 3-hydroxy 6-nitro chroman: SR 47025
(A+B=—CH=CH—CH=CH—; X=C—NO$_2$; $R_1$=CN; $R_2$=H; $R_3$=OH)

A solution containing 2.7 g of 2-cyanamino pyridine, 3 g of 2,2-dimethyl 3,4-epoxy 6-nitro chroman in 50 ml of tetrahydrofuran and 0.2 ml of triethylamine is heated at reflux for 96 hours. The mixture is allowed to cool and is then filtered. The precipitate is washed with ethyl ether, followed by water and acetone and dried. 250 mg of the expected product are obtained.
Mp=253° C.

EXAMPLE 3

4-(2-Cyanimino 1,2-dihydro 1-pyridyl) 2,2-dimethyl 6-nitro chromene: SR 47063
(A+B=—CH=CH—CH=CH—; X=C—NO$_2$; $R_1$=CN; $R_2$++$R_3$=double bond)

This compound is prepared starting from the chromanol obtained in example 2.

30 mg of sodium hydride are added in small portions to 400 mg of SR 47025 placed in 50 ml of tetrahydrofuran. After 96 hours at room temperature, the reaction mixture is concentrated to dryness and the residue is taken up in 50 ml of water. It is extracted twice with methylene chloride, then the extracts are dried and evaporated to dryness. 250 mg of product are obtained which are purified by chromatography on a column of silica using a methylene chloride-methanol (99.5/0.5 v/v) mixture as eluant.

80 mg of the expected product are recovered.
Mp=257° C.

EXAMPLE 4

Trans 3-acetyloxy 4-(2-cyanimino 1,2-dihydro 1-pyridyl) 2,2-dimethyl 6-nitro chroman: SR 47601
(A+B=—CH=CH—CH=CH—; X =C—NO$_2$; $R_1$=CN; $R_2$=H; $R_3$=OCOCH$_3$)

5 g of SR 47025, obtained in example 2 are mixed with 25 ml of pyridine, 3.8 ml of acetic anhydride are added and the mixture is stirred at room temperature for 4 hours. The mixture is taken up in ethyl acetate, then washed with acidified water and dilute bicarbonate solution. The product which precipitates is filtered off, washed with ethyl ether then dried at 100° C. in a vacuum. 5.2 g of the expected product are obtained.
Mp=232° C.

EXAMPLE 5

4-(2-Cyanimino 1,2-dihydro 1-pyridyl) 2,2-dimethyl 6-nitro chromene: SR 47063 (idem. ex. 3)

A mixture containing 5 g of SR 47061, obtained in example 4, in 100 ml of toluene is heated at reflux for 3 hours in the presence of 2.8 ml of diazabicycloundecene. The reaction mixture is filtered at room temperature and the product obtained is washed with toluene and ethyl ether. The product obtained (4.1 g) is recrystallized from 200 ml of alcohol and 3 g of the expected product are obtained.
Mp=257° C.

EXAMPLE 6

Trans 6-acetyl 4-(2-cyanimino 1,2-dihydro 1-pyrimidyl) 2,2-dimethyl 3-hydroxy chroman: SR 47141
(A+B=—CH=CH—CH=N—; X=—COCH$_3$; R$_1$=CN; R$_2$=H; R$_3$=OH)

2-Cyanamino pyrimidine is prepared according to the British patent 860 423.

SR 47141 is obtained according to the method described in example 1.
Mp=254° C.

EXAMPLE 7

Trans 4-(2-cyanimino 1,2-dihydro 1-pyrimidyl) 2,2-dimethyl 3-hydroxy 6-nitro chroman: SR 47162
(A+B=—CH=CH—CH=N—; X=C—NO$_2$; R$_1$=CN; R$_2$=H; R$_3$=OH)

This compound is prepared according to the procedure described in example 6.
Mp=316° C.

EXAMPLE 8

Trans 4-(2-cyanimino 1,2-dihydro 1-pyridyl) 2,2-dimethyl 3-hydroxy 6-trifluoroacetyl chroman: SR 47140 (A+B=—CH=CH—CH=CH—; X=COCF$_3$; R$_1$=CN; R$_2$=H; R$_3$=OH)

This compound is prepared according to the method described in example 1.
Mp=218° C.

EXAMPLE 9

Trans 6-cyano 4-(1,2-dihydro 2-nitrimino 1-pyridyl) 2,2-dimethyl 3-hydroxy chroman: SR 47159
(A+B=—CH=CH—CH=CH—; X=C—CN; R$_1$=NO$_2$; R$_2$=H; R$_3$=OH)

The pyridiylnitramine is prepared according to the method described in J. Am. Chem. Soc., 1955, 77, 3154.

The compound of example 9 is obtained by following the procedure of example 2.
Mp=279° C.

EXAMPLE 10

Trans 4-(2-cyanimino 1,2-dihydro 1-pyridyl) 3,4-dihydro 2,2-dimethyl 3-hydroxy pyrano[3,2-c]pyridine: SR 47142 (A+B=—CH=CH—CH=CH—; X=N; R$_1$=CN; R$_2$=H; R$_3$=OH)

This compound is obtained starting from the epoxide (II) in which X=N and 2-cyanamino pyridine.
Mp=171° C.

EXAMPLE 11

4-(2-cyanimino 1,2-dihydro 1-pyridyl) 2,2-dimethyl pyrano[3,2-c]pyridine; SR 47320
(A+B=—CH=CH—CH=CH—; X=N; R$_1$=CN; R$_2$+R$_3$=double bond)

A mixture of SR 47142, prepared in the previous example, 0.6 g of tetrahydrofuran and 50 mg of sodium hydride is maintained at reflux for 5 hours. The reaction mixture is concentrated, taken up in water, washed, dried and concentrated to give 0.45 g of a yellow solid. Chromatography on silica is then performed using a methylene chloride-methanol mixture (99/1, v/v) as eluant. 90 mg of the expected product are recovered.
Mp=256° C.

EXAMPLE 12

4-(2-cyanimino 1,2-dihydro 1-pyridyl) 6-cyano 2,2-dimethyl chromene: SR 47164
(A+B=—CH=CH—CH=CH—; X=C—CN; R$_1$=CN; R$_2$+R$_3$=double bond)

A) Trans 4-(2-cyanimino 1,2-dihydro 1-pyridyl) 6-cyano 2,2-dimethyl 3-hydroxy chroman: prepared as in Example 1
B) SR 47164

80 mg of sodium hydride are added in small portions to 1 g of the previously prepared chromanol placed in 50 ml of anhydrous tetrahydrofuran. After 2 hours at reflux, the reaction mixture is evaporated to dryness and the residue is taken up in 100 ml of water. It is extracted twice with methylene chloride, then the extracts are dried and evaporated to dryness. 600 mg of product are obtained which are purified by chromatography on a column of silica using a methylene chloride-methanol mixture (99.5/0.5 - v/v) as eluant.

400 mg of the expected product are recovered.
Mp=292° C.

EXAMPLE 13

Trans 2,2-dimethyl 3-hydroxy 4-(2-methanesulfonimino 1,2-dihydro 1-pyridyl) 6-nitro chroman: SR 47195
(A+B=—CH=CH—CH=CH—; X=C—NO$_2$; R$_1$=CH$_3$—SO$_2$—; R$_2$=H; R$_3$=OH)

A solution of 4.7 g of 2-amino pyridine in 6.3 ml of pyridine is cooled to 0° C. and 5.75 g of methyl chloride are added dropwise. The reaction mixture is stirred for 1 hour at 0° C., then for 24 hours at room temperature. The solidified reaction mixture is poured into 20 ml of water and stirred in order to break up the precipitate. After begin filtered off, the solid product recovered is recrystallized from water. 6.7 g of 2-methanesulfonimino pyridine are obtained.
Mp=204° C.

The usual procedure involving reaction of the product obtained with 2,2-dimethyl 3,4-epoxy 6-nitro chroman is then employed in order to obtain the expected product.
Mp=265°-267° C.

EXAMPLE 14

Trans 2,2-dimethyl 3-hydroxy 4-(1,2-dihydro 2-nitrimino 1-pyridyl) 6-nitro chroman; SR 47174
(A+B=—CH=CH—CH=CH—; X=NO$_2$; R$_1$=NO$_2$; R$_2$=H; R$_3$=OH)

The compound is prepared as in example 9.
Mp=269° C.

EXAMPLE 15

Trans 4-(1,2-dihydro 2-methylimino 1-pyridyl) 2,2-dimethyl 3-hydroxy 6-nitro chroman; SR 47220
(A+B=—CH=CH—CH=CH—; X=C—NO$_2$; R$_1$=CH$_3$; R$_2$=H; R$_3$=OH)

500 mg of SR 47174, prepared in the previous example and 50 ml of methylamine are mixed in a 30% ethanol solution and left at room temperature for 3 days. The insoluble material is filtered off, the solvents are evaporated, the residue is taken up in ethyl ether, the precipitate is dissolved and the insoluble material is filtered off. The ethereal phase is washed with water and dried over sodium sulfate. The residue is taken up in hot isopropyl ether, then the expected product crystallizes.

m = 60 mg.
Mp = 155° C.

EXAMPLE 16

Trans 4-[1,2-dihydro 2-(2-trifluoromethyl phenyl)sulfonimino 1-pyridyl]2,2-dimethyl 3-hydroxy 6-nitro chroman: SR 47281

(A+B=—CH=CH—CH=CH—; X=C—NO$_2$;

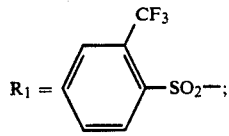

R$_2$=H; R$_3$=OH)

0.94 g of 2-amino pyridine in 5 ml of pyridine are cooled to 0° C., 2.5 g of 2-trifluoromethyl phenylsulfonyl chloride are added and the mixture is stirred overnight at room temperature. The reaction mixture is poured into water and extracted with methylene chloride. The organic phase is washed with water, then dried over sodium sulfate and evaporated to dryness in a vacuum. The solid residue is taken up in ethyl acetate and filtered. 2 g of 2-(2-trifluoromethyl phenyl)sulfonimino pyridine are obtained in the form of a white solid.

Mp = 218°–220° C.

SR 47281 is then prepared by reaction with 2,2-dimethyl 3,4-epoxy 6-nitro chroman according to the method described in the previous examples.

Mp = 305° C.

EXAMPLES 17 TO 35

Other compounds according to the invention were prepared by using the procedure described in the previous examples. These compounds are presented in the tables 1 and 2 below.

TABLE 1

(I)

| SR No. Example No. | Z | R$_1$ | R$_4$, R$_5$ | R$_3$ | M.p. °C. |
|---|---|---|---|---|---|
| 47163 17 | NO$_2$ | H | H, H | OH | 184 |
| 47219 18 | CN | CF$_3$ | H, H | OH | 233 |
| 47282 19 | CN | CN | Cl, H | OH | 314 |
| 47283 20 | CN | CN | H, CH$_3$ | OH | 268 |
| 47321 21 | CN | OCH$_3$ | NO$_2$, H | OH | 164 |
| 47416 22 | NO$_2$ | CN | H, CH$_3$ | OH | 292 |

TABLE 1-continued (I)

| SR No. Example No. | Z | R$_1$ | R$_4$, R$_5$ | R$_3$ | M.p. °C. |
|---|---|---|---|---|---|
| 47417 23 | CN | CN | CH$_3$, H | OH | 309 |
| 47433 24 | NO$_2$ | OH | H, H | OH | 219 |
| 47599 25 | NO$_2$ | NO$_2$ | H, H | OCOCH$_3$ | 237 |
| 47601 26 | NO$_2$ | CN | H, H | OCOCH$_3$ | 235 |
| 47602 27 | COCF$_3$ | CN | H, H | OCOCH$_3$ | 125 |
| 47603 28 | Br | CN | H, H | OH | 277 |
| 47604 29 | Br | CN | H, H | OCOCH$_3$ | 217 |
| 47605 30 | CH$_3$ | CN | H, H | OCOCH$_3$ | 218 |

TABLE 2

| SR No. Example No. | Z | R$_1$ | M.p. °C. |
|---|---|---|---|
| 47319 31 | CN | CN | 252 |
| 47600 32 | NO$_2$ | NO$_2$ | 237 |
| 47617 33 | COCF$_3$ | CN | 190 |
| 47618 34 | Br | CN | 250 |
| 48259 35 | NH$_2$ | CN | 266 |

We claim:
1. Compound of formula:

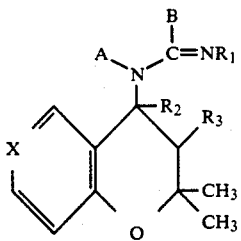

in which:
- A and B are linked together between N and C=NR₁ and represent a —CH=CR₄—CR₅=CH— group, one of the substituents $R_4$ or $R_5$ denoting hydrogen, the other being selected from hydrogen, halogen, nitro or $C_1$-$C_4$ alkyl;
- X represents a C—Z group;
- Z represents hydrogen, halogen, $C_1$-$C_4$ alkyl, cyano, nitro, acetyl or trifluoroacetyl, phosphono or dialkoxyphosphoryl, the alkyl group being a $C_1$-$C_3$ group or an amino group;
- $R_1$ represents hydrogen, cyano, nitro, $C_1$-$C_4$ alkyl, hydroxyl, $C_1$-$C_4$ alkoxy, trifluoroacetyl, methanesulfonyl, benzenesulfonyl unsubstituted or substituted on the phenyl by methyl, halogen or trifluoromethyl;
- $R_2$ represents hydrogen;
- $R_3$ represents hydroxyl or acetyloxy or $R_2$ and $R_3$ together form a bond.

2. Compound according to claim 1, of formula (I), in which:
- $R_1$ represents CN,
- X represents a C—NO₂ group or a C—CN group,
- A and B represent a —CH=CR₄—CR₅=CH— group and
- $R_2$ and $R_3$ together form a bond.

3. 4-(2-cyanimino 1,2-dihydro 1-pyridyl)2,2-dimethyl 6-nitro chromene.

4. 4-(2-cyanimino 1,2-dihydro 1-pyridyl)6-cyano 2,2-dimethyl chromene.

5. A pharmaceutical composition having an antihypertensive and/or antiarrhythmic effect which comprises an effective amount of one compound of formula (I) according to claim 1 in admixture with a pharmaceutically acceptable excipient.

6. A pharmaceutical composition according to claim 5 wherein the effective amount is 0.01 to 2 mg of active ingredient per dosage unit.

7. A pharmaceutical composition having an antihypertensive and/or antiarrhythmic effect which comprises an effective amount of one compound of formula (I) according to claim 2 in admixture with a pharmaceutically acceptable excipient.

8. A pharmaceutical composition according to claim 7 wherein the effective amount is 0.01 to 2 mg of active ingredient per dosage unit.

9. A pharmaceutical composition having an antihypertensive and/or antiarrhythmic effect which comprises an effective amount of one compound of formula (I) according to claim 3 in admixture with a pharmaceutically acceptable excipient.

10. A pharmaceutical composition according to claim 9 wherein the effective amount is 0.01 to 2 mg of active ingredient per dosage unit.

11. A pharmaceutical composition having an antihypertensive and/or antiarrhythmic effect which comprises an effective amount of one compound of formula (I) according to claim 4 in admixture with a pharmaceutically acceptable excipient.

12. A pharmaceutical composition according to claim 11 wherein the effective amount is 0.01 to 2 mg of active ingredient per dosage unit.

13. A method of treating a human or animal subject suffering from hypertension or arrhythmia comprising administering a pharmaceutically effective amount of a compound according to claim 1 to the human or animal subject.

14. A method according to claim 13, wherein the compound is administered orally, buccally, sublingually, subcutaneously, intramuscularly, intravenously or rectally.

15. A method according to claim 14, wherein the effective amount is 0.01 to 2 mg per kg of body weight administered 1 to 5 times per day.

* * * * *